United States Patent [19]

Aoshiro

[11] 4,241,729
[45] Dec. 30, 1980

[54] ENDOSCOPE WITH GAS-TIGHT CAP PERMITTING PRESSURIZATION

[75] Inventor: Hisatake Aoshiro, Tokyo, Japan

[73] Assignee: Machida Endoscope Co., Ltd., Tokyo, Japan

[21] Appl. No.: 926,748

[22] Filed: Jul. 21, 1978

[30] Foreign Application Priority Data

Aug. 4, 1977 [JP] Japan .......................... 52-103847[U]

[51] Int. Cl.³ .............................................. A61B 1/00
[52] U.S. Cl. ...................................... 128/4; 356/241
[58] Field of Search ........................................ 128/3-8; 350/96.20, 96.26; 73/40, 45.5, 46; 356/241; 134/21, 22 C

[56] References Cited

U.S. PATENT DOCUMENTS

| 1,335,073 | 3/1920 | Osborn | 73/45.5 |
|---|---|---|---|
| 2,761,311 | 9/1956 | Baker | 73/46 |
| 3,023,607 | 3/1962 | Bolch et al. | 73/46 |
| 3,425,419 | 2/1969 | Dato | 128/303.1 |
| 3,690,769 | 9/1972 | Mori | 350/96.26 |
| 3,866,599 | 2/1975 | Johnson | 128/6 X |
| 3,956,011 | 5/1976 | Carleton | 128/350 R X |
| 3,963,438 | 6/1976 | Banez | 134/22 C |
| 3,995,934 | 12/1976 | Nath | 350/96.1 |
| 4,066,070 | 1/1978 | Utsugi | 128/4 |

FOREIGN PATENT DOCUMENTS 2062178 6/1972 Fed. Rep. of Germany .............. 128/4

Primary Examiner—Robert W. Michell
Assistant Examiner—Jeffrey W. Tayon
Attorney, Agent, or Firm—Peter L. Berger

[57] ABSTRACT

The present invention discloses herewith an endoscope by which pressurized air is led into an inner portion of the endoscope. A plug of a light-transmitting optic bundle tube which communicates with the inner portion is covered, partially or totally, by a gas-tight cap which has a pressure inlet. The pressurized air is led from the pressure inlet into the inner portion of the endoscope through a terminal part or a gap of the plug.

By these provisions, an internal pressure of the endoscope is raised to an extent not smaller than the external pressure of a cleanser in order to prevent the cleanser from flowing into the inner portion of the endoscope when washing and/or sterilizing a non-waterproof endoscope. In addition, a pinhole on a flexible sheath can easily be detected by testing a leakage of the pressurized air as for a waterproof endoscope.

4 Claims, 4 Drawing Figures

ENDOSCOPE WITH GAS-TIGHT CAP PERMITTING PRESSURIZATION

BACKGROUND OF THE INVENTION

A. Field of the Invention

The present invention relates to an endoscope for observing and/or treating a body cavity, or more particularly, to an endoscope by which a pressurized air is led into the inner portion of it.

B. Description of the Prior Art

An endoscope is a medical instrument which is employed for observing and/or treating a body cavity and an inner portion as well as an external portion of it should be kept clean.

Accordingly, a body fluid, cleanser or disinfectant should be prevented from flowing into, for example, an inner portion of a grip end. On the top of it, the endoscope should be necessarily dipped in a washtub after use for washing and/or sterilizing the external portion of it.

There are two types of endoscopes in view of waterproof structure, a waterproof endoscope and a non-waterproof one. The waterproof structure is not provided to a gap of parts, for example, an angle deflector dial which not only communicates with the inner portion of the endoscope but also protrudes to the external surface in case of non-waterproof endoscope. On the contrary, a waterproof structure such as a seal by a packing is provided to the gap of parts in case of waterproof endoscope.

A cleanser or disinfectant flows into the inner portion of the grip end when washing above-said non-waterproof endoscope in the washtub and then the endoscope is contaminated. Moreover, the body fluid or the filth flows into the inner portion through a pinhole or a crack on the flexible sheath even if the waterproof endoscope is perfectly sealed and also the inner portion is contaminated.

To attack above-said problems, it is necessary to raise the internal pressure of the non-waterproof endoscope in order to prevent the cleanser from flowing into the inner portion when washing and/or sterilizing it. In addition, it is also necessary to detect the pinhole or crack of the waterproof endoscope before utilizing it. But, the necessary steps have not been taken for the problems.

SUMMARY OF THE INVENTION

The present invention aims at an improvement of an endoscope by which a pressurized air is led into the inner portion of it. A plug of a light-transmitting optic bundle which communicates with the inner portion is covered, partially or totally, by a gas-tight cap which has a pressure inlet. Pressurized air is led from the pressure inlet into the inner portion through a terminal part or a gap of the plug.

It is a first object of the invention to prevent a cleanser from flowing into the inner portion of the non-waterproof endoscope. To achieve the object, the internal pressure of the endoscope is raised to an extent not smaller than the external pressure of the cleanser when washing and/or sterilizing the endoscope.

It is a second object of the invention to detect the pinhole on the flexible sheath of the waterproof endoscope easily by testing a leakage of the pressurized air.

The above and further objects and novel features of the invention will more fully appear from the following detailed description when the same is read in connection with the accompanying drawings. It is to be expressly understood, however, that the drawings are for purpose of illustration only and are not intended as a definition of the invention.

DETAILED DESCRIPTION OF PREFERRED EMBODIMENTS

Figure 1:
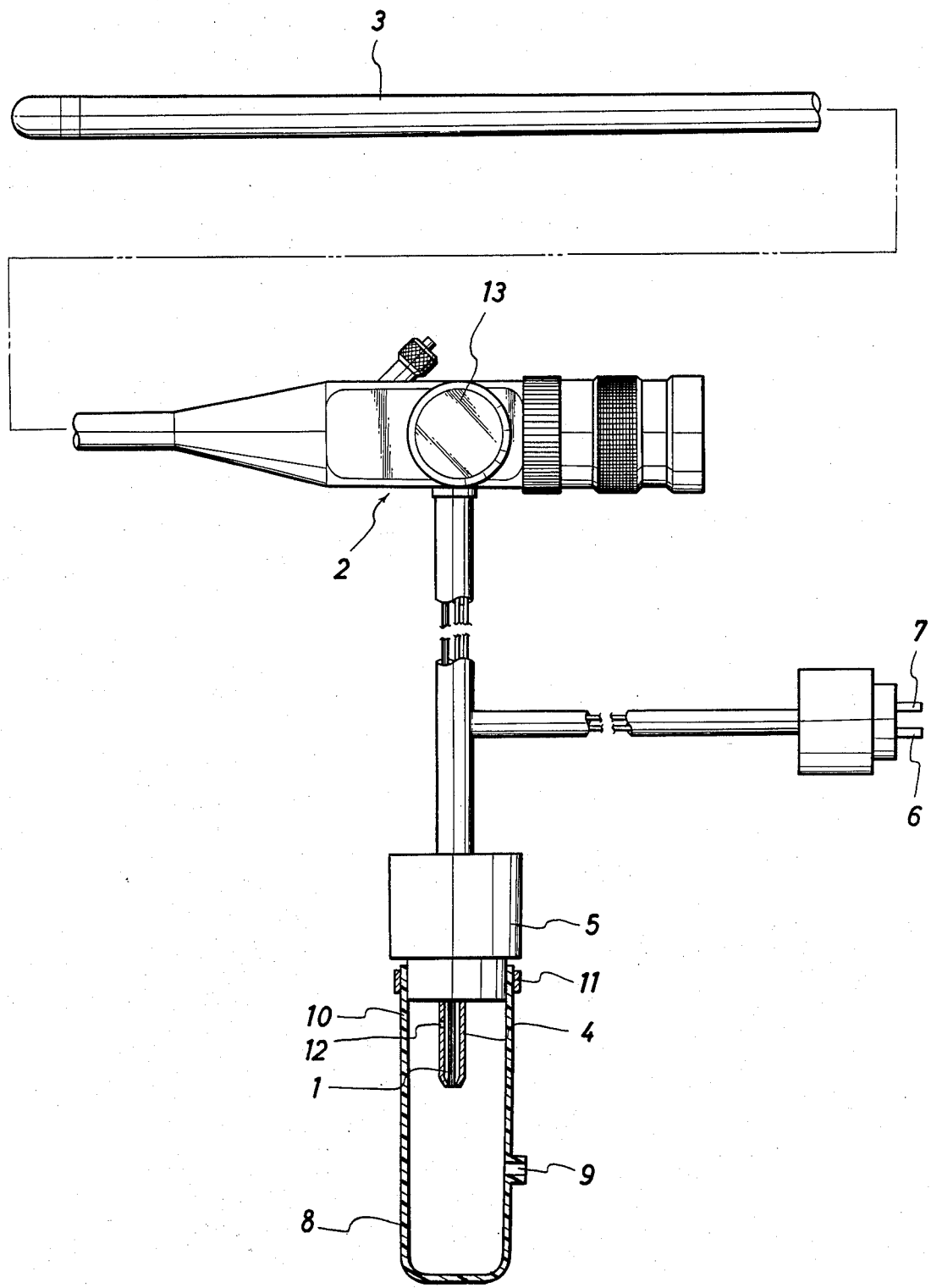
FIG. 1 is a partial cross-sectional view of an endoscope illustrating an embodiment of the present invention.
Figure 2:
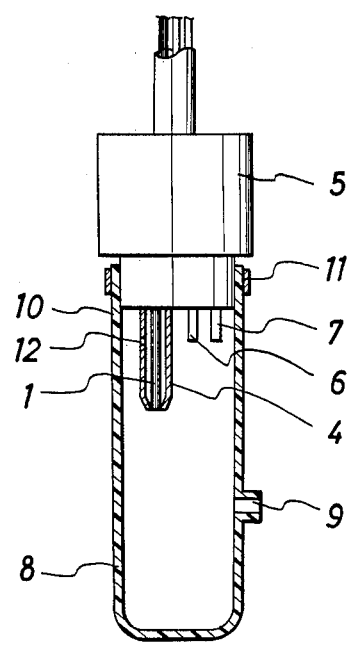
FIG. 2 is a partial cross-sectional view of an endoscope in which an air feeding pipe is provided in the plug shown in FIG. 1.

An embodiment of the present invention is now described with reference to FIGS. 1 and 2. In the figures, numeral 1 indicates a light-transmitting optic bundle for transmitting an observing light from a light source (not shown) to an object in a body cavity via a grip end 2 and a flexible sheath 3. Numeral 4 indicates an optic bundle tube for protecting the optic bundle 1. Numeral 5 indicates a plug for connecting an optic bundle tube 4 with the light source. An air feeding pipe 6 and/or a water feeding pipe 7 may be provided in the plug 5 as shown in FIG. 2. Numeral 8 indicates a gas-tight cap which has a pressure inlet 9 and is shaped like a pouch with a rubber, a synthetic resin or a metal. An open end 10 of the gas-tight cap 8 is attached to the plug 5. Numeral 11 indicates a clasp for fixing the open end 10 movably. Numeral 12 indicates an aperture which may be provided at a suitable point of the plug 5, if needed. Numeral 13 indicates an angle deflector dial for manipulating the flexible sheath 3.

In the next place, the operation of the above-said endoscope is respectively described regarding a non-waterproof endoscope and a waterproof one.

Pressurized air is led from the pressure inlet 9 of the gas-tight cap 8 when washing and sterilizing the non-waterproof endoscope in a washtub. Then, the pressurized air enters into the inner portion of the endoscope via a gap of the plug 5 and/or the aperture 12 to raise the internal pressure of the endoscope. Thereby, the cleanser is prevented from flowing into the inner portion, for example, from the gap of the angle deflector dial 13.

As for the waterproof endoscope, the pressurized air is led into the inner portion from the pressure inlet 9 in order to detect a pinhole on the flexible sheath 3 in a washtub and a leakage of the pressurized air indicates the presence of the pinhole. The pressurized air must be led from the pressure inlet 9 after choking up the air feeding pipe 6 and the water feeding pipe 7 in case of an embodiment of FIG. 2.

Figure 3:
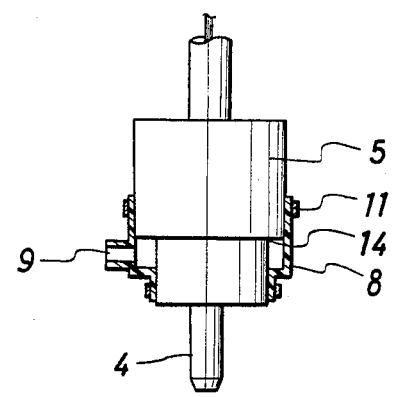
FIG. 3 is a partial cross-sectional view of an endoscope illustrating another embodiment of the present invention.
Figure 4:
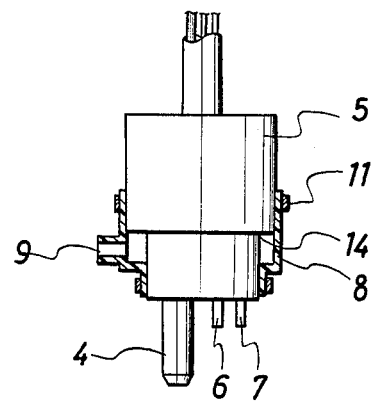
FIG. 4 is a partial cross-sectional view of an endoscope in which an air feeding pipe is provided in the plug shown in FIG. 3.

Referring now to FIGS. 3 and 4, another embodiment of the present invention is now described. In the figures, numeral 5 indicates a plug of an optic bundle tube 4, numeral 6 indicates an air feeding pipe, numeral 7 indicates a water feeding pipe. Numeral 8 indicates a gas-tight cap with a pressure inlet 9 and is shaped like a ring whose both ends are open and a gap 14 of the plug 5 is covered by the cap 8. Numeral 11 indicates a clasp for fixing both ends of the gas-tight cap 8 to the plug 5. As with the before-said embodiment, the pressurized air is led into the inner portion of the endoscope from the pressure inlet 9 of the gas-tight cap 8 via the gap 14 and the same operation as described is obtained.

By the way, an observation of a body cavity may often be effected in a state that the cavity is expanded by an air fed from the air feeding pipe. The internal pressure of the endoscope according to the present invention may be raised in compliance with the pressure of the body cavity, therefore, a body fluid or filth is prevented from flowing into the inner portion of the endoscope by balancing the internal pressure of the endoscope against that of the body cavity.

As described above, the present invention is applicable both to the non-waterproof endoscope and the waterproof endoscope and has various uses. Moreover, the gas-tight cap is attached to the plug of the optic bundle tube which is not contaminated by the body fluid because it is separated from the patient. Accordingly, it is not necessary to wash the plug after washing the gas-tight cap, therefore, handling is convenient.

Further, cost for production is inexpensive because the gas-tight cap can easily be attached to the plug.

While there have been shown and described and pointed out the fundamental novel feature of the invention as applied to preferred embodiments, it will be understood that the various omissions and substitutions and changes in the form and details may be made by those skilled in the art without departing from the spirit of the invention

What is claimed is:

1. An endoscope comprising a grip end, an elongated sheath adapted to fit into a body orifice having a distal end and a proximal end, a fiber optic bundle extending from said proximal end to said distal end of said sheath, said grip end connected with said sheath and said sheath terminating in an examining end, said endoscope including said sheath having a closed inner cavity portion, the portions of said endoscope forming the walls of said closed cavity being non-expandable, said cavity extending along a major portion of said sheath, said sheath being flexible, a plug enabling a light source to be connected with said fiber optic bundle, a gas flow path through said plug permitting gas to flow therethrough and being in air communication with said closed inner cavity portion, a gas-tight cap having a gas inlet means in air communication with said gas flow path through said plug, and a source of pressurized gas connected to said gas inlet means to introduce pressurized gas into said closed inner cavity portion to be contained therein, whereby said pressurized gas prevents cleansing liquid on the outside of said endoscope from permeating said sheath and highlights pinholes in said sheath by the production of fluid bubbles thereat.

2. An endoscope combination as set forth in claim 1, wherein said gas-tight cap comprises a pouch shape having a mouth end, said mouth end being securely attached to said plug.

3. An endoscope combination as set forth in claim 1, comprising an optical bundle tube enclosing said fiber optic bundle within said cap, said optical bundle tube having an aperture in air communication with said closed inner cavity potion of said endoscope.

4. An endoscope combination as set forth in claim 1, wherein said gas inlet means is integrally formed in said cap.

* * * * *